(12) United States Patent
Ogura

(10) Patent No.: US 6,652,465 B2
(45) Date of Patent: Nov. 25, 2003

(54) BLOOD-PRESSURE MEASUREMENT APPARATUS CAPABLE OF HEART FUNCTION ASSESSMENT

(75) Inventor: Toshihiko Ogura, Komaki (JP)

(73) Assignee: Colin Corporation, Komaki (JP)

( * ) Notice: Subject to any disclaimer, the term of this patent is extended or adjusted under 35 U.S.C. 154(b) by 1 day.

(21) Appl. No.: 10/142,908

(22) Filed: May 13, 2002

(65) Prior Publication Data
US 2002/0188209 A1 Dec. 12, 2002

(30) Foreign Application Priority Data
Jun. 6, 2001 (JP) ........................................ 2001-171493

(51) Int. Cl.[7] ................................................ A61B 5/02
(52) U.S. Cl. ........................................ 600/490; 600/493
(58) Field of Search ................................ 600/490, 492, 600/493, 494, 495, 496, 499, 500, 509, 50

(56) References Cited

U.S. PATENT DOCUMENTS

| | | | | |
|---|---|---|---|---|
| 5,301,675 A | * | 4/1994 | Tomita | 600/485 |
| 5,853,371 A | * | 12/1998 | Inukai et al. | 600/483 |
| 6,346,083 B1 | * | 2/2002 | Nishibayashi et al. | 600/490 |
| 6,450,966 B1 | * | 9/2002 | Hanna | 600/490 |

* cited by examiner

Primary Examiner—Max F. Hindenburg
Assistant Examiner—Navin Natnithithadha
(74) Attorney, Agent, or Firm—Oliff & Berridge, PLC

(57) ABSTRACT

An apparatus for blood pressure measurement capable of heart function assessment for readily putting on a living subject, comprising an inflatable cuff including a pressure-pulse-wave sensor, which is combined into one body with the cuff at an upper-stream side end of the cuff, when wrapped around an upper-arm portion, so as to detect, at the upper-stream side than a blood-flow stopped position, the pressure-pulse-wave, which is of the same waveform as an aorta waveform while blood-flow is stopped, and an ejection time calculating means (a heart function parameter calculating means), by which an ejection time ET can be calculated as a time difference from a rising-point to a dicrotic notch of the pressure-pulse waveform for heart function assessment. Since a blood pressure BP also can be measured with the cuff, all the putting on the living subject, that is needed to measure the blood pressure and heart-function is to put on the cuff, which is combined with the pressure-pulse wave sensor, and to wrap the cuff around the upper-arm portion, therefore, putting-on becomes more simple and easier for measuring a heart function parameter and a blood pressure.

7 Claims, 6 Drawing Sheets

BLOOD-PRESSURE MEASUREMENT APPARATUS CAPABLE OF HEART FUNCTION ASSESSMENT

BACKGROUND OF THE INVENTION

1. Field of the Invention

The present invention relates in general to a blood-pressure measurement apparatus capable of heart function assessment.

2. Related Art Statement

In order to diagnose a state of circulating system, a blood pressure is conventionally measured. Although a heart is one of circulatory organs, it is difficult to assess a heart function, only by measuring the blood pressure. Sometimes it is needed to assess the heart function as well as the blood pressure.

In order to assess a heart function of a living subject, such heart function parameters are calculated as an ejection time, which is an actual period of ejecting blood from the heart, a pre-ejection period, which is a period from a start of cardiac muscle activity to actual starting of blood ejection, and a cardiac mechanical efficiency. These parameters can also be calculated based on a waveform of an aorta pressure-pulse. For example, the ejection time can be calculated based on a period from a rising point of an aorta pressure-pulse-waveform to a dicrotic notch of the same. Also, the pre-ejection period can be calculated based on a period from a Q-wave appearing point of an electrocardiogram to the rising point of the aorta pressure-pulse-waveform.

However, since the aorta pressure-pulse-waveform is difficult to be detected non-invasively, apparatus for assessing the heart function have been proposed, wherein the aorta pressure-pulse-waveform is estimated from an arterial pressure-pulse-waveform measured at another position in the living subject, and the heart function parameters are calculated. For example, apparatus in JP-A-11-113860, JP-A-2000-333910 and JP-A-2000-333911, which have been filed by the present applicant and laid open in public, are such apparatus. According to the apparatus in the Publications, an aorta pressure-pulse-waveform is estimated based on a radial artery pressure-pulse-waveform detected at a wrist and then, based on the estimated aorta pressure-pulse-waveform, heart function parameters are calculated. Also, at the apparatus, blood pressure can be measured as well as heart function parameters.

However, as for the apparatus noted in the applications, it is needed to adapt an inflatable cuff to be wrapped around an upper-arm portion, to put a radial pressure-pulse-wave detecting probe, internally containing a pressure-pulse-wave sensor, on the wrist, to stick a plurality of detecting electrodes of electrocardiograph on predetermined points of living subject, and further to place a heart-sound microphone in the vicinity of a heart. It is considerably cumbersome to put on these devices. Therefore, such apparatus is desirable that can more easily assess heart function as well as can measure a blood pressure. Especially, for the recent growing importance of medical care at home, such apparatus is desirable that can readily measure heart function as well as a blood pressure at home.

SUMMARY OF THE INVENTION

It is therefore an object the present invention to provide a blood-pressure measurement apparatus capable of heart function assessment, which is easy to put on.

After extensive studies to achieve the object, the present inventor discovered following fact that is, when a blood-flow in an artery of an upper-arm portion is stopped with such cuff as used for blood pressure measurement, a pressure-pulse waveform, detected at an upper stream side of the blood-flow stopped position, is the same waveform as an aorta pressure-pulse-waveform, therefore, if a pressure-pulse wave sensor is combined with the cuff, and if pressure-pulse-wave sensor is used to detect the pressure-pulse waveform while the blood-flow in the upper-arm portion is stopped with the cuff, it is possible to put on the cuff for blood pressure measurement and, at the same time, the sensor for detecting the aorta pressure-pulse-waveform. This invention is developed based on this fact.

According to the first invention, there is provided a blood-pressure measurement apparatus comprising (a) a variable pressure and blood-flow stopping cuff to be wrapped around an upper-arm portion of a living subject, that measures a blood pressure of the living subject by changing a pressing pressure of the cuff according to a predetermined speed, the apparatus comprising a blood-flow-stopping means for stopping blood-flow at the upper-arm portion with the cuff, (b) a pressure-pulse wave sensor equipped being combined with the cuff so as to detect a pressure-pulse-wave, appearing at an upper-stream side of the blood-flow stopped position and, (c) a heart function parameter calculating means for calculating a heart function parameter of the living subject, based on the detected pressure-pulse wave at the upper-stream with the sensor, while the cuff is stopping the blood-flow in an artery of the upper-arm portion.

According to the first invention, since the pressure-pulse wave sensor detects upper-stream than the blood-flow stopped position by the cuff, a pressure-pulse waveform, which is detected with the pressure-pulse wave sensor while the cuff stops the blood-flow in the artery of upper-arm portion by blood-flow stopping means, is the same waveform as an aorta-waveform. Therefore, the heart function parameter can be calculated with a heart function parameter calculating means based on the pressure-pulse wave detected with the sensor. Also, a blood pressure can be measured with the same cuff that is wrapped around the upper-arm portion. As a result, decreased number of devices to be put on the living subject leads to readily putting-on for the measuring the heart function parameter and a blood pressure.

The second invention in order to achieve the object is that the heart function parameter calculating means calculates an ejection time ET from a time of a pressure-pulse wave rising-point to a dicrotic notch of the pressure-pulse wave of the upper-stream detected by the pressure-pulse wave sensor.

According to the second invention, the ejection time ET can be calculated only from the pressure-pulse-wave, which is detected by the pressure-pulse wave sensor, which is combined with the cuff, and any other sensor is not needed to be put on to detect other signals of the living subject than pressure-pulse wave sensor. So it leads to easy device putting-on for heart function parameter measurement.

According to the third invention in order to achieve the object, the apparatus according to the first or second invention further comprises (a) a plurality of electrodes to be adapted to stick on predetermined positions of the living subject, and (b) an electrocardiograph to detect, via the electrodes, an electro-cardiac signal representing activity-potential of cardiac muscle, wherein the heart-function parameter calculating means calculates a pre-ejection period PEP, as a time difference, that is, a period of time, from Q-wave detected time of the electro-cardiac signal, which is detected via the electrodes by the electrocardiograph, to the time of the rising-point of pressure-pulse-wave, which is detected by the pressure-pulse wave sensor.

As for the apparatus according to the filed patent application JP-A-11-113860, in order to measure an ejection time, a cuff, pressure-pulse wave sensor and a heart-sound microphone are needed to be put on the living subject and, in order to measure a pre-ejection period of time, a plurality of electrodes, equipped with the electro-cardiograph, in addition, have to be put on the living subject. On the other hand, according to the present invention, in order to measure the ejection time and the pre-ejection period, all the devices that have to be put on the living subject are the cuff and a plurality number of electrodes.

According to the fourth invention in order to achieve the object, the heart function calculating means calculates a cardiac mechanical efficiency, which is one of heart function parameters, as a ratio of an aorta effective elastance Ea to a left ventricle tele-systolic elalastance, based on a ratio of the pre-ejection period PEP to the ejection time ET.

According to the fifth invention, the apparatus comprises a plurality number of the pressure-pulse-wave sensors, which are arranged in a lengthwise direction at an inner peripheral face of the cuff so as to assure sufficient sensitivity.

According to the sixth invention, the pressure-pulse-wave sensor comprises a plurality number of pressure-sensitive semiconductor elements, which are arranged in a lengthwise direction at a pressing face of the pressure-pulse-wave sensor. And the apparatus of the first invention further comprises an optimum detective element determining means for selecting a most appropriate element from a plurality number of pressure-sensitive semiconductor elements.

According to the present invention, it is preferable that the blood-flow stopping means should be such, that a pressing pressure of cuff is increased at a predetermined quick speed to reach a predetermined blood-flow stopping pressure, which is a sufficient pressure to stop a blood flow in the artery of the upper-arm portion, and thereafter, is maintained for predetermined period of time and then, the cuff pressure is decreased at a predetermined slow speed. Thus, while the cuff pressure is maintained at the blood-flow stopping pressure, heart function parameters can be calculated, and also in the course of slowly decreasing cuff pressure, the blood pressure measurement can be performed. Therefore, by increasing a cuff pressure only one time, both blood pressure and heart function parameters can be calculated.

BRIEF DESCRIPTION OF THE DRAWINGS

The above and optional objects, features, and advantages of the present invention will be better understood by reading the detailed description of the preferred embodiments of the invention when considered in conjunction with the accompanying drawings, in which.

DETAILED DESCRIPTION OF THE PREFERRED EMBODIMENTS

Hereinafter, there will be described an embodiment of the present invention in detail by reference to the accompanying drawings.

Figure 1:
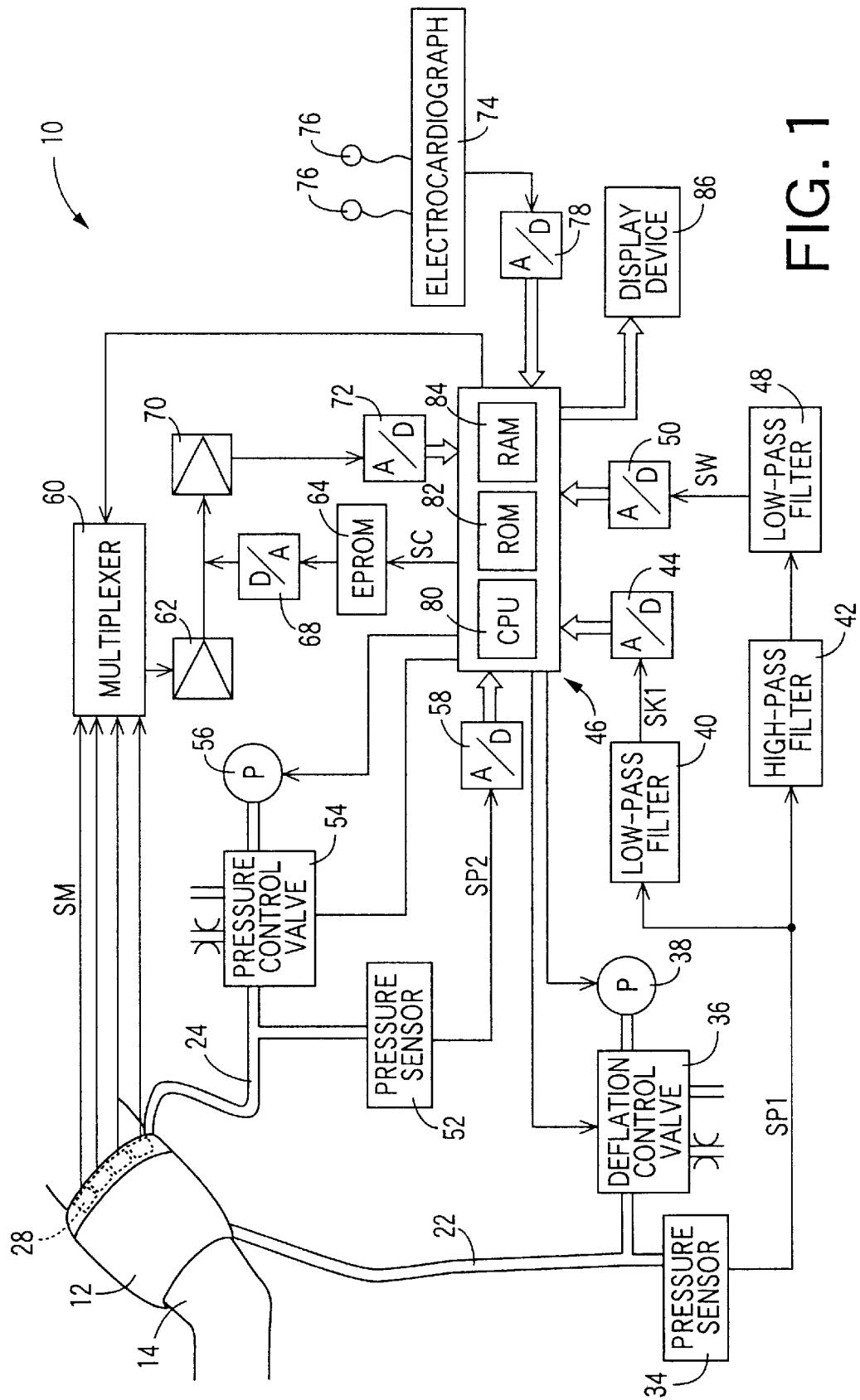
FIG. 1 is a diagrammatic view illustrating a circuit structure of a blood-pressure measurement apparatus of the present invention.

FIG. 1 is the diagrammatic view for explaining a circuit construction of the blood-pressure measurement apparatus 10 capable of heart function assessment.

Figure 2:
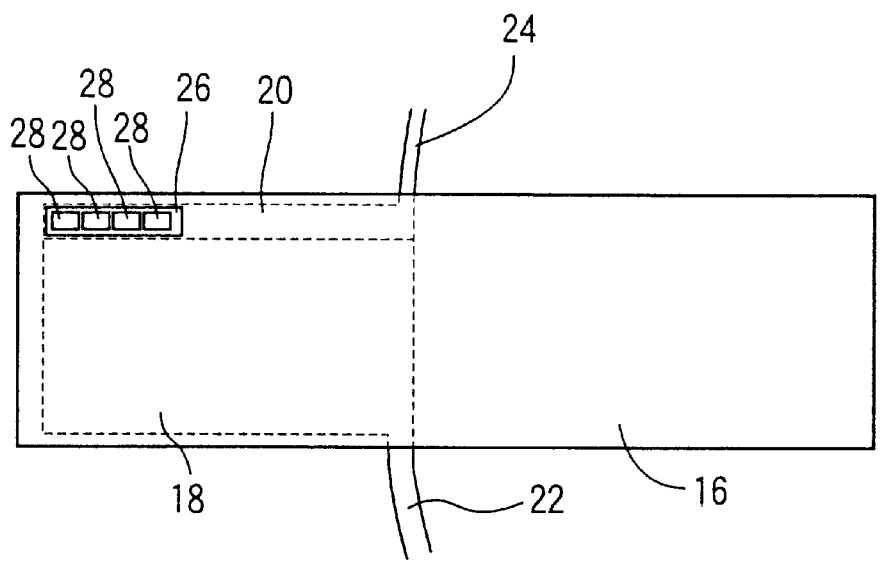
FIG. 2 is a development view of an inflatable cuff of FIG. 1.

In FIG. 1, reference numeral 12 designates the inflatable cuff, which is, for example, wrapped around the upper-arm portion 14 of a right arm of a patient. The inflatable cuff 12 is wholly covered with a belt-like bag 16 as shown in FIG. 2, which is a development view of the inflatable cuff 12. The belt-like bag 16 is made of non-stretchable cloth and has substantially the same length in a lengthwise direction as that of a conventional cuff used for a blood pressure measurement wrapped around the upper-arm portion, However, a width of the cuff 12 is larger than that of the conventional cuff by a dimension corresponding to a width of a small-bag 20, which will be explained hereinafter.

Inside the belt-like bag 16, there are provided a large-bag 18 of the approximately same length in the lengthwise direction as a peripheral length of the upper-arm portion 14, 24 cm for example, and also the small-bag 20. These large-bag 18 and small-bag 20 are made of rubber. The large-bag 18 is for blood pressure measurement and, has substantially the same width as that of a rubber bag employed in the conventional cuff for blood pressure measurement. The small-bag 20 is for pressing a pressure-pulse-wave-sensor 28 (to be explained hereinafter) to an artery of the upper-arm portion 14 with predetermined pressure and has smaller width than that of the large-bag, for example, 2 cm. The large-bag 18 and the small-bag 20 are placed so that respective one long side thereof is adjacent to each other. In a state, in which the cuff 12 is wrapped around the upper-arm portion 14, the small-bag 20 is placed at the upper-end in the wrapping axis direction. Each of large-bag 18 and small-bag 20 is connected to respective piping 22 or 24 for supplying pressurized air thereto.

The belt-like bag 16 is provided with a flexible support plate 26, which has substantially the same width as that of small-bag 20 and is fixed to an inner peripheral face of the cuff 12 that contacts the upper-arm portion 14 when the cuff 12 is wrapped around the same 14. More specifically described, the flexible support plate 26 is fixed to an inner surface of the cuff 12 that corresponds to the small bag 20, so that when the cuff 12 is wrapped around the upper-arm portion 14, the flexible support plate 26 is pressed by the small-bag 20. The flexible support plate 26 is provided with four pressure-pulse-wave sensors 28, which are fixed along a straight line to a lengthwise direction of cuff 12. Spacing between each pair of adjacent sensors should be relatively small, 0.9 mm for example. Thus, since the cuff 12 is equipped and is combined with the pressure-pulse wave sensors 28 the pressure-wave pulse sensors 28 are put on the upper-arm portion 14 simultaneously, when the cuff 12 is wrapped around the upper-arm portion. Also, the pressure-pulse-wave sensors 28 are located in such position as to be pressed by the small-bag 20 at the inner peripheral face of the cuff 12 and the small-bag 20 is placed at the upper-stream side than the large-bag 18, therefore, in a state, in which the blood-flow in the artery of upper-arm portion 14 is stopped by the large-bag 18, the pressure-pulse-wave sensors 28 are pressed by predetermined pressure corresponding to a pressure of small-bag 20 for detecting the pressure-pulse-wave that appears at the upper stream side than the blood-flow stopped position.

Figure 3:
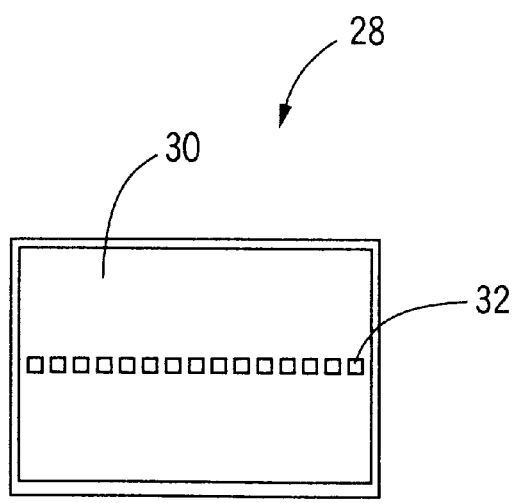
FIG. 3 is a plan view of a pressure-pulse wave sensor.

FIG. 3 is a plan view of one of the four pressure-pulse wave sensors 28. Each of pressing faces 30 of the pressure-pulse-wave sensors 28 is composed has semiconductor chip, which is made of mono-crystalline silicone and is, for example, about 13 mm long in a lengthwise direction of cuff 12 (i.e., in a left-right direction in FIG. 3). In the pressing face 30, a number of semiconductor pressure sensitive elements 32 are arranged along a straight line in a lengthwise direction with a predetermined spacing. In the present embodiment, each pressure-pulse-wave sensor 28 has fifteen semiconductor pressure sensitive elements 32 which are arranged at a regular spacing interval of 0.2 mm.

Back to FIG. 1, the large-bag 18 is, via the piping 22, connected to a pressure sensor 34, a deflation control valve 36 and an air pump 38. The deflation control valve 36 is selectively placed in four positions, that is, a pressure-supply position, in which the deflation control valve 36 permits pressurized air to be supplied from the air pump 38 into the large-bag 18, a slow-deflation position, in which the deflation control valve 36 permits the pressurized air to be slowly discharged from the large-bag 18, a quick-deflation position, in which the deflation control valve 36 permits the pressurized air to be quickly discharged from the large-bag 18, and a pressure-maintain position, in which the deflation control valve 36 permits to maintain the pressure inside the large-bag 18.

The pressure sensor 34 detects a pressure in the large-bag 18 and supplies a first pressure signal SP1, representing the pressure, each to a low-pass filter 40 and to a high-pass filter 42, via an amplifier, (not shown). The low-pass filter 40, from the pressure signal SP1, extracts a static pressure component SK1 contained in the signal SP1, which represents a pressing pressure of the large-bag 18. And the large-bag pressing pressure signal SK1 is supplied to an electronic-control device 46 via an A/D (analog-to-digital) converter 44. On the other hand, from the first pressure signal SP1, which is supplied to the high-pass filter 42, the high-pass filter 42 extracts only a higher frequency component, not lower than 0.8 Hz, for example, and supplies thus extracted frequency component signal to a low-pass filter 48 via an amplifier (not shown). The low-pass filter 48 passes only a lower frequency component, for example, not higher than 10.8 Hz. The signal, which passed through the low-pass filter 48, represents a cuff pulse-wave signal SW, which is an oscillatory component of the pressure signal SP1 and the cuff pulse-wave signal SW is supplied, via an A/D converter 50, to the electronic-control device 46.

The small-bag 20 is connected to a pressure-sensor 52, a pressure control valve 54 and an air pump 56 respectively via the piping 24. The pressure-sensor 52 detects an air pressure PK2 in the small-bag 20,and supplies a second pressure signal SP2, representing the detected pressure PK2 inside the small-bag 20, to the electronic-control device 46 via an A/D converter 58. The pressure-control valve 54 adjust a pressure of pressurized-air from the air pump 56 according to a signal from the electronic-control device 46 and supplies thus adjusted pressurized-air to the small-bag 20.

A multiplexer 60 sequentially supplies, according to a switching signal SC supplied from the electronic control device 46, the respective pressure-pulse-wave signal SM supplied from the sixty pressure sensitive elements 32 of the four pressure-pulse wave sensors 28, each signal SM for a predetermined time, to an amplifier 62. An EPROM (erasable programmable ROM) 64 stores, for the sixty pressure sensitive elements 32, respective correction signals for eliminating respective individual sensitivity differences among the pressure sensitive elements 32, and sequentially supplies, according to the signal SC, supplied from the electronic control device 46, i.e., in synchronism with the respective switching operations of the multiprex 60, the respective correction signals, to a D/A (digital to analog) converter 68, in such a manner that the respective correction signals SC sequentially correspond to the respective pressure sensitive elements 32 supplying the respective pressure-pulse-wave signals SM being currently dealt with by the multiplexer 60.

Each of the sixty pressure-pulse-wave signals SM that have been amplified by the amplifier 62, and a corresponding one of the sixty correction signals that have been converted to respective analog signals by the D/A converter 68 are supplied to an amplifier 70. Thus, the sixty corrected pressure-pulse-wave signals SM supplied to the amplifier 70 have a uniform sensitivity. Each of the sixty corrected pressure-pulse-wave signals SM is supplied to an I/O (input-output-port) port (not shown) of the electronic control device 46 via an A/D converter 72.

An electrocardiograph 74 (a) is provided with a plurality of electrodes 76 to be stuck on the surface skin of the living subject, located surrounding the heart of the living subject, (b) detects the action potential of cardiac muscle via the electrodes 76, and (c) supplies the electro-cardiac signal SE representing the action potential of cardiac muscle, via A/D converter 78, to the electronic-control device 46.

The electronic-control device 46 is a so-called microcomputer, which is equipped with a CPU (central processing unit) 80, a ROM (read only memory) 82, and a RAM (random access memory) 84. The CPU 80 processes signals according to a control program pre-stored in the ROM 82, and by utilizing a temporary-storage function of the RAM 84, so as (a) to control the deflation control valve 36 and the air-pump 38 for measuring a blood pressure, (b) to control the pressure-control valve 54 and the air-pump 56 for the detection of pressure-pulse wave SM, (c) to determine blood pressure values BP, (d) to calculate heart function parameters, and (e) to control a display device 86 to display thus determined blood pressure values BP and heart function parameters.

Figure 4:
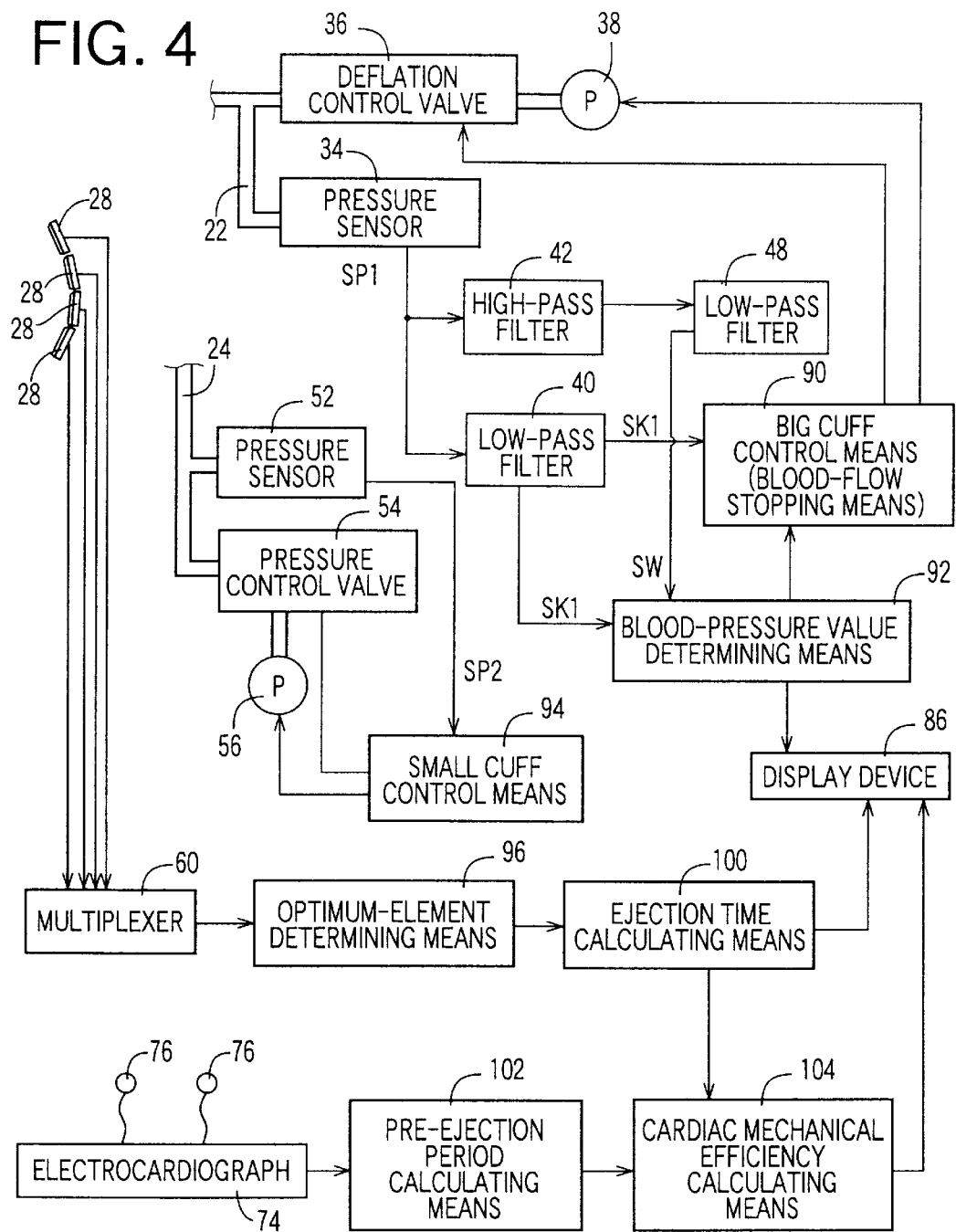
FIG. 4 is a block diagram for illustrating essential control functions of an electronic control device of the blood-pressure measurement apparatus of FIG. 1.

FIG. 4 is a function block diagram, which explains essential control functions of the electronic-control device 46. In FIG. 4, a large-bag-pressure control means 90, which also functions as a blood-flow stopping means, that is, controls the deflation control valve 36 and the air pump 38. As a means for stopping the blood flow completely in the artery of upper-arm portion 14, the pressing pressure of the large-bag 18 is quickly increased up to a predetermined blood-flow-stopping pressure PM1, (about 180 mm/Hg, for example), and is maintained at the blood-flow stopping pressure PM1 level, for a period of a pulse or a plurality of pulses, then the pressure is slowly decreased at a speed of about 2~3 mmHg/sec. After a blood pressure determining means 92 determines blood pressure values BP, the large-bag pressure control means 90 decreases the pressing pressure down to the atmospheric pressure.

Based on the change of a cuff-pulse-wave signal SW, which is obtained during the slow deflation process of the pressing pressure of large-bag 18 by the large-bag-pressure control means 90, the blood pressure determining means 92 determines a systolic blood pressure $BP_{SYS}$, a mean blood pressure $BP_{MEAN}$, and a diastolic blood pressure $BP_{DIA}$ of the living subject according to well-known oscillometric method, and controls the display device 86 to display thus determined blood pressure values.

A small-bag pressure control means 94, according to the second pressure signal SP2 supplied from the pressure sensor 52, controls the pressure-control valve 54 and the air-pump 56 to increases the air pressure PK2 inside the small-bag 20 up to a predetermined target pressure PM2 and then maintains the pressure PK2 at the target pressure PM2. The target pressure PM2 is determined, based on experiments, so as to assure a sufficient sensitive pressing pressure for detecting the pressure-pulse-wave by the pressure-pulse-wave sensor 28. The controlling of the pressure PK2 of the small-bag 20 by the small-bag control means 94 is performed, while the pressure of large-bag 18 is controlled by the large-bag control means 90 and the blood-flow in the upper-arm portion 14 is stopped.

Figure 5:
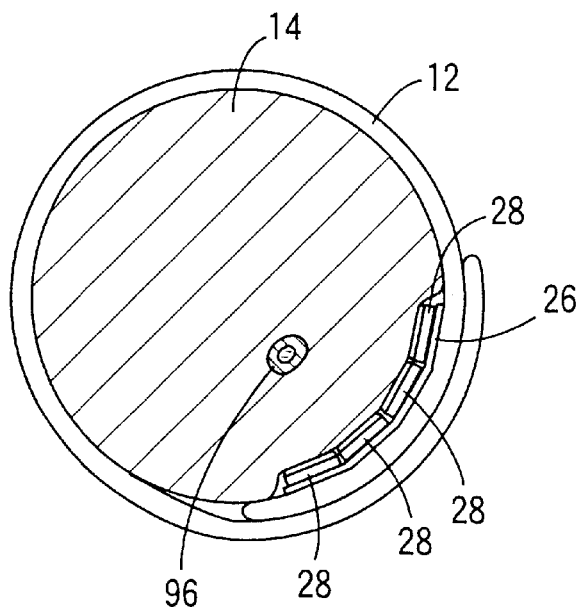
FIG. 5 is a cross-section view for explaining a state, in which the inflatable cuff is wrapped around an upper-arm portion of a living subject.
Figure 6:
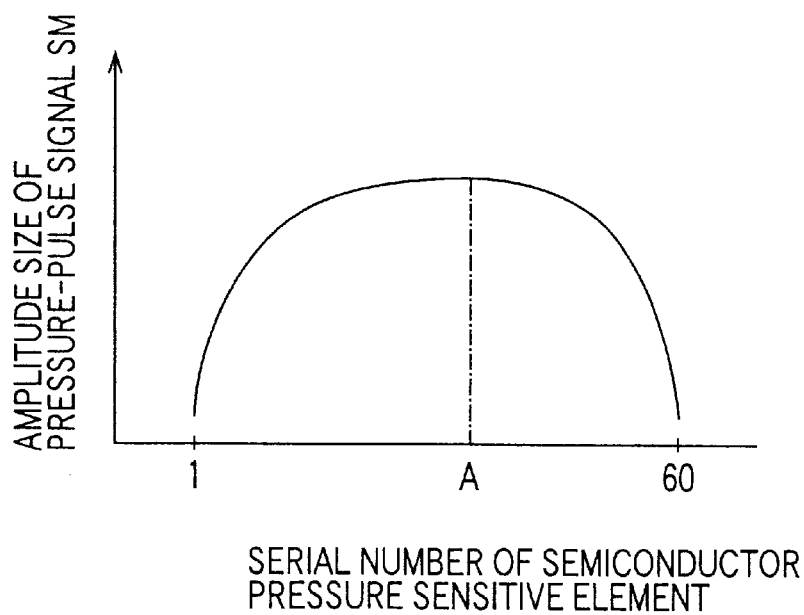
FIG. 6 is a graph showing a relationship between individual semiconductor pressure-sensitive-elements and respective amplitudes of respective pressure-pulse-wave signals (SM), generated by the individual semiconductor pressure-sensitive elements.

The optimum-detective element determining means 96 selects, from the sixty pieces of semiconductor pressure sensitive elements 32 of the four pressure-pulse-wave sensors 28, an optimum semiconductor pressure sensitive element 32 that is the most appropriate to detect a pressure-pulse-wave (hereinafter referred to as the optimum detective element A, i.e. active element). FIG. 5 is a cross-section view to explain a state of the cuff 12 wrapped around the upper-arm portion 14, wherein as shown in FIG. 5, distances from a brachial artery 98 inside the upper-arm portion to the pressure-pulse-wave sensors 28, that is, to the semiconductor pressure-sensitive elements 32 provided at the pressing face 30 of each pressure-pulse wave sensor 28 are different each other. Therefore, it is desirable that one of semiconductor pressure-sensitive elements 32, which is placed at the nearest to the brachial artery 98, that is, the semiconductor-pressure sensitive element, which is placed right above, or in the vicinity of, the brachial artery 98, should be selected as the optimum detective element A to detect, with the highest sensitivity, the pressure-pulse-wave. FIG. 6 shows, as an example, a relationship between the semiconductor pressure sensitive elements 32 and respective amplitudes of the pressure-pulse-wave signals SM detected by the elements 32. In FIG. 6, semiconductor sensitive element numbers shown at the horizontal axis are the sequential numbers from an end-located element of semiconductor sensitive elements 32, which are arranged in a straight line. Respective amplitudes of the pressure-pulse-wave SM, detected by relatively nearer pressure sensitive elements 32 to the brachial artery 98, are relatively greater than those detected by the relatively more remote elements from the brachial artery 98. Therefore, the optimum detective element determining means 96, for example, selects as the optimum detective element A, the semiconductor pressure sensitive element 32, which has detected the relatively greater, most preferably, the greatest amplitude of pressure-pulse-wave signal SM in the relationship shown in FIG. 6.

Figure 7:
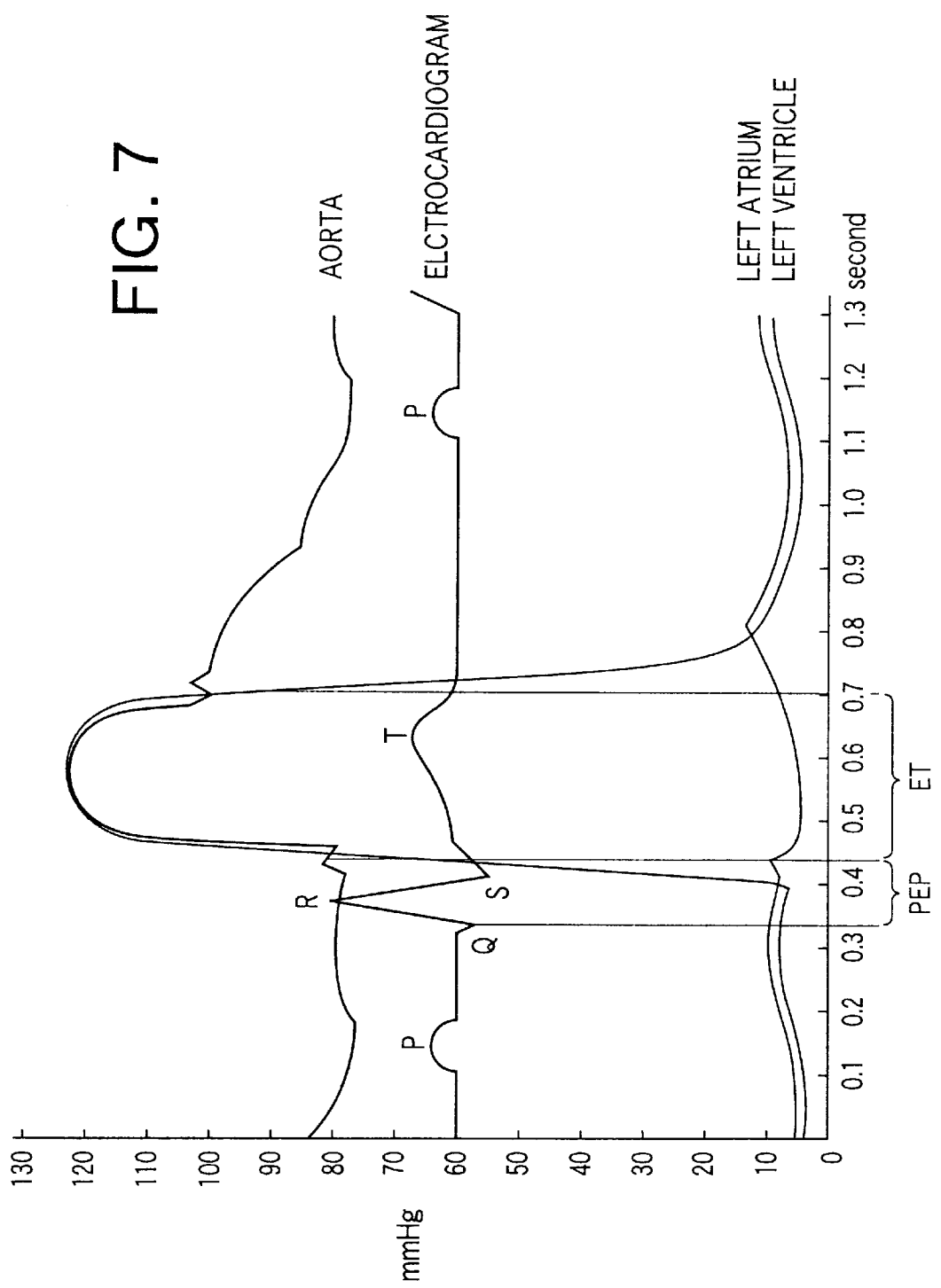
FIG. 7 is a graph for typically representing each pressure of an aorta, a left atrium and a left ventricle, and a cardiogram.

An ejection time calculating means 100 calculates a ejecting period of time, or an ejection time ET, while the pressurized air of large-bag 18 is controlled at the blood-flow-stopping pressure PM1 by the large-bag control means 90, i.e., while the large-bag 18 stops the blood-flow in the upper-arm portion 14, the blood ejection time ET of a left ventricle is calculated based on a pressure-pulse-waveform detected by the optimum detective element A. In a state, in which the blood flow in the upper-arm portion 14 is stopped by the large-bag 18, a pressure-pulse wave, which is detected by the pressure-pulse wave sensors 28, provided at an upper-stream than the large-bag 18, can be regarded as an aorta pressure-pulse-waveform. Also, as indicated in FIG. 7, which typically shows each blood pressure at an aorta, at a left atrium and at a left ventricle together with an electrocardiogram, the ejection time ET can be calculated as a time difference from an appearing time of a rising point of an aorta pressure waveform to an appearing time of a dicrotic notch. Therefore, the ejection time ET can be calculated based on the pressure-pulse-waveform, which is detected by the optimum detective element A, while the blood-flow in the upper-arm portion 14 is stopped by the large-bag 18. Since the ejection time ET is one of a heart function parameters, the ejection time calculating means 100 functions as a calculating means for calculating the heart function parameter.

A pre-ejection period calculating means 102 calculates a pre-ejection period PEP, which is a period from a time when cardiac muscle of the left ventricle started contraction and to a time when blood is ejected from the left ventricle. The pre-ejection period PEP is calculated, while the large-bag 18 is stopping the blood-flow in the artery of upper-arm portion 14, as a time difference, or a period time from a Q-wave appearing time at the electrocardiogram which shows an electro cardiac signal SE supplied from the electrocardiograph 74, to an appearing time of rising point of pressure-pulse-wave which is detected by the optimum detective element A. Since the pre-ejection period PEP is also one of heart function parameters, the pre-ejection period calculating means 102 works also as heart function parameter calculating means.

A cardiac mechanical efficiency calculating means 104 calculates a ratio of an effective elastance of the aorta Ea to a telesystolic elastance of the left ventricle Ees, which ratio is defined as a cardiac mechanical efficiency Ea/Ees. The cardiac mechanical efficiency can be calculated according to a Formula 1 as noted in detail at the Publication JP-A-11-113860. Therefore, the cardiac mechanical efficiency calculating means 104 calculates the cardiac mechanical efficiency Ea/Ees by substituting the pre-ejection period PEP and the ejection time ET, which have been calculated by the pre-ejection period calculating means 102 and the ejection time calculating means 100 respectively, into the Formula 1.

$$Ea/Ees = PEP/ET \quad \text{Formula 1}$$

Figure 8:
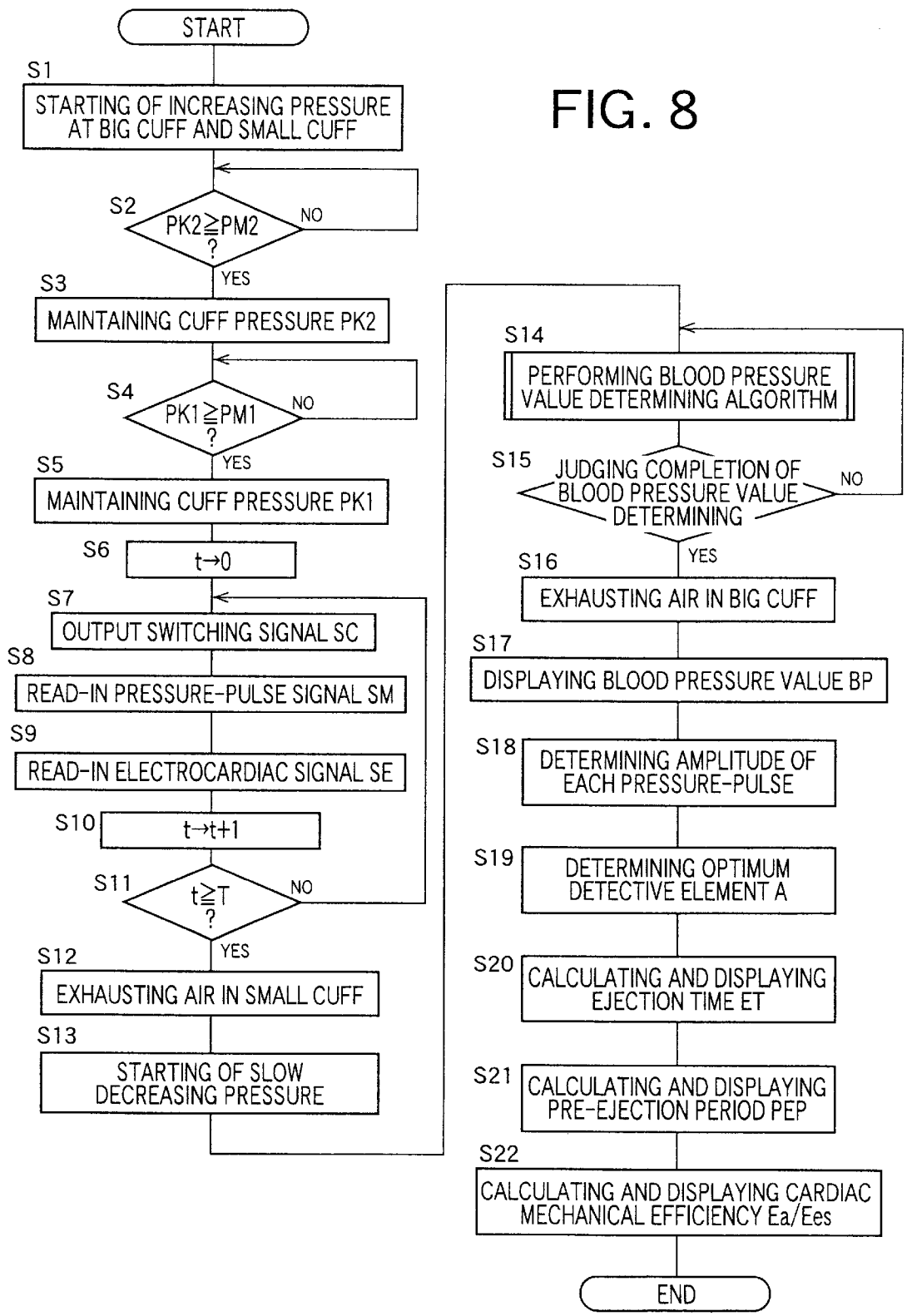
FIG. 8 is a control-action flow chart for explaining further specifically the function block diagram of FIG. 4 of the electronic control device.

FIG. 8 is a flow chart in order to explain further details of the electronic-control device 46, which has been shown at FIG. 4, the function block diagram.

First, at Step S1 in FIG. 8, (hereinafter, 'Step' is omitted.) the electronic-control device 46 starts the air pump 38 and switches the deflation control valve 36 to the pressure supply position, so that an air pressure inside the large-bag 18 is started for quick increase, and simultaneously by operating the air pump 56, an air pressure inside the small-bag 20 is started for increase.

Next, at S2, the air pressure PK2 inside the small-bag 20 is judged, whether it reached to the predetermined level of 20~30 mmHg or more, or not. As long as a negative judgment of S2 is made, the judgment of S2 is repeated and pressure increasing for the large-bag 18 and small-bag 20 is continued. On the other hand, if a positive judgment of S2 is made, then, the control goes to S3 and by controlling the pressure control valve 54, the pressure PK2 of the small-bag 20 is maintained at the predetermined level.

Next, at S4, the pressure PK1 inside the large-bag 18 is judged, whether it reached to the predetermined blood-flow stopping pressure PM1 of 180 mmHg or more, or not. If a negative judgment of S4 is made, pressure increasing for the large-bag is continued, and also the judgment of S4 is repeatedly performed. On the other hand, if a positive judgment of S4 is made, the control goes to S5, in which, by switching the pressure deflation control valve 36 to the pressure-maintain position, the pressure PK1 in the large-bag 18 is maintained at the pressure.

Next, at S6, the electronic control device 46 resets a number counted by timer t to zero, and at S7, a switching signal SC is output, so that the multiplexer 60 and EPROM 64 can be switched in a sufficiently shorter cycle time than an average pressure-pulse-wave cycle time. Next at S8, the pressure-pulse wave signal SM, which is supplied from multiprexer 60, is read in. Further, at S9, the electro-cardiac signal SE, which is supplied from the electro cardiograph 74 is read in.

Next, at S10, the electronic control device 46 adds one to the number counted by the timer t; and in the next S11, the judgment is performed, whether timer t has reached a predetermined reading-in cycle time T or more, or not. This reading-in cycle time T is predetermined, for example, as one cycle time of an average pulse. When a negative judgment of S11 is made, the steps of the S7~S11 are repeated. By each repeating of S7~S11, an EPROM (erasable programmable ROM) sequentially supplies, according to the switching signal SC supplied from the electronic control device 46, i.e., in synchronism with the respective switching operation of the multiplex 60, the respective correction signals, to a D/A (digital-to-analog) converter 68, in such a manner, the pressure-pulse wave signals SM by one pulse and the electro cardiac signal SE are read in.

If a positive judgment of S11 is made, all necessary signals for calculating heart function have been read in, so, the control goes to next S12 and stops the air pump 56 and, by controlling the control-valve 54, inside of the small-bag 20 is exhausted. In the flowchart FIG. 8, S1~S3 and S12 correspond to the small-bag pressure control means 94. At next S13, the air pump 38 is stopped and also the deflation control-valve 36 is switched to the slow-deflation position so as to start decreasing slowly an air pressure of the large-bag PK1.

Next at S14, that corresponds to the blood pressure determining means 92, an algorism for determining blood pressure values is performed, that is, during the slow pressure decreasing process of the large-bag 18, amplitudes of the cuff pulse-wave represented by pulse-wave signals SW, which are sequentially supplied from the low-pass filter 48, are determined by each pulse. And based on a change of the amplitude, the well-known oscillometric system algorism is performed for determining a systolic blood pressure $BP_{SYS}$, a mean blood pressure $BP_{MEAN}$, and a diastolic blood pressure $BP_{DIA}$.

Next at S15, it is judged whether determinations have been completed, or not. At S15, it is judged whether the systolic blood pressure $BP_{SYS}$, the mean blood pressure $BP_{MEAN}$ and the diastolic blood pressure $BP_{DIA}$. are determined, or not. In the beginning of this measurement, the negative judgments are made, then, the steps from the S14 are repeatedly performed.

On the other hand, if a positive judgment of S15 is made, the control goes to S16. The deflation control-valve 36 is switched to the quick deflation position and an air inside the large-bag 18 is quickly exhausted to decrease the pressure. At the flow chart in FIG. 8, S1, S4~S6, S11, S13 and S16 correspond to the large-bag pressure control means 90. Next at S17, the systolic blood pressure $BP_{SYS}$, the mean blood pressure $BP_{MEAN}$ and the diastolic blood pressure $BP_{DIA}$, which have been determined at S14, are displayed at the display device 86.

Next, S18~S19, which correspond to the optimum detective element determining means 96, are performed. At S18, amplitudes of respective pressure-pulse-wave signals SM are determined, which have been read during the repeating of S7~S11. In the next S19, the greatest amplitude is selected from the amplitudes, which have been determined at S18, and the semiconductor pressure sensitive element 32, which detected the greatest amplitude, is determined as the optimum detective element A.

Next, S20, which corresponds to an ejection time calculating means 100, is performed. At S20, among the read-in pressure-pulse-wave signals in the repeating of S7~S11, the pressure-pulse-wave signal SM, which has been detected by the optimum detective element A at S19, is analyzed in order to determine a rising point and an appearing time of a dicrotic notch in the pressure-pulse-wave signal SM. And a time difference, or a period, from a rising point appearing time to a dicrotic notch appearing time is determined as an ejection time ET. Thus calculated ET is displayed at the display device 86. As the rising point, such point is used, (a) that an amplitude increasing rate indicates the greatest value, (b) that a differentiated waveform, obtained by a differentiated pressure-pulse-wave, shows the maximum value, or (c) a point that the value of a one fifth of the pulse-pressure is indicated. The last value (c) is used because noises around the minimum point of the pulse wave cause relatively greater influence and it is difficult to determine the appearing point with accuracy.

Next, S21, which corresponds to the pre-ejection period calculating means 102, is performed. At S21, (a) an electro-cardiac signal SE, which is read in by repeating of S7~S11, is analyzed, (b) a Q-wave appearing time is determined at the electrocardiogram, which the electro-cardiac signal SE is representing, and (c) a pre-ejection period PEP is calculated as a time difference, or a period of time, from the Q-wave appearing time which has been determined at the S20 to a rising point appearing time of the pressure-pulse-wave. (d) Thus calculated pre-ejection period PEP is displayed at the display device 86.

Next, S22, which corresponds to the cardiac mechanical efficiency calculating means 104, is performed, that is, at S22, the pre-ejection period PEP, which has been obtained at S21, is divided by the ejection time ET, which has been obtained at S20, to calculate the cardiac mechanical efficiency Ea/Ees. Thus calculated result is displayed as a cardiac mechanical efficiency at the display device 86.

In this embodiment, since the pressure-pulse-wave sensor 28 detects the pressure-pulse-wave, which is appearing at upper-stream side than the upper-arm portion 14 where the blood-flow is stopped by the large-bag 18, the pressure-pulse waveform detected by the pressure-pulse sensor 28, is the same waveform as the aorta waveform, in the state, in which the large-bag 18 is stopping the blood-flow in the upper-arm portion 14 at S5 (the large-bag pressure control means 90, or the blood-flow stopping means). Therefore, at S20 (the ejection time calculating means 100), at S21 (the pre-ejection period calculating means 102) and at S22 (the cardiac mechanical efficiency calculating means 104), based on the pressure-pulse-wave, the heart function parameters, i.e., the ejection time ET, the pre-ejection period PEP and the cardiac mechanical efficiency Ea/Ees can be calculated. Also, blood pressure values BP can be measured with the large-bag 18 wrapped around the upper-arm portion 14. Therefore, since the number of devices to be put on the living subject is decreased, the putting-on becomes more simple and easier for measurement of the heart function parameter and of the blood pressure.

Also, according to the embodiment, the ejection time ET is calculated as the period of time from the rising-point of pressure-pulse-wave and to the dicrotic notch, which are detected by the pressure-pulse-wave sensor 28, and the pre-ejection period PEP is calculated as the period of time from the Q-wave detected time by the electrocardiograph 74 to the rising-point of pressure-pulse-wave detected by the pressure-pulse-wave sensor 28, therefore, all the devices that is needed to be put on the living subject for measuring the ejection time ET and pre-ejection period PEP, are the cuff 12 and the electrodes 76.

Also, according to the embodiment, while the pressing pressure of the large-bag 18 is maintained at the blood-flow stopping pressure PM1, based on the pressure-pulse-waveform detected by the pressure-pulse-wave sensor 28, heart function parameters (the ejection time ET, the pre-ejection period PEP and the cardiac mechanical efficiency, Ea/Ees) can be calculated. Also, in the process of slowly decreasing the pressing pressure of large-bag 18, blood pressure values BP can be measured, therefore, by increasing the pressing pressure of large-bag 18 only once, blood pressure values BP and heart function parameters can be calculated.

While presently preferred embodiments of the present invention have been described above with a certain degree of particularity, by reference to the accompanying drawings, it is to be understood that the invention is not limited to the details of the illustrated embodiments, but may be otherwise embodied.

For example, as the heart function parameter, the blood-pressure measurement apparatus 10 calculates the ejection time ET, the pre-ejection period PEP and the cardiac mechanical efficiency Ea/Ees, however, it may calculate the ejection time ET only. In case that only the ejection time ET is calculated, such sensor as electrodes 76, in order to detect other signal than pressure-pulse wave of the living subject, is not needed to be put on the living subject, so it is further more simple and easier to put on the device to measure heart function parameter.

Also, the blood-pressure measurement apparatus 10 calculates as heart function parameter, the ejection time ET, the pre-ejection period PEP and the cardiac mechanical efficiency Ea/Ees, however, other heart function parameter such as, a left ventricle tele-systolic elastance Ees, an aorta effective elastance Ea and etc. may be calculated.

Also, the blood-pressure measurement apparatus 10 is composed to measure a blood pressure according to oscillometric method, however, it may be composed according to so-called Korotkoff auscultation method, wherein each cuff pressure of Korotkoff-sound appearing time and disappearing time is determined as the systolic and diastolic blood pressure, respectively.

Also a pressure source of the blood-pressure measurement apparatus 10 is composed of air pumps 38 and 56, however, it may be other pressure source, such as $CO_2$ cylinder.

It is to be understood that the present invention may be embodied with other changes, improvements, and modifications that may occur to a person skilled in the art without departing from the spirit and scope of the invention defined in the appended claims.

What is claimed is:

1. A blood-pressure measurement apparatus provided with a variable-pressure and blood-flow stopping cuff which is adapted to be wrapped around an upper-arm portion of a living subject, that measures a blood pressure of said living subject by changing pressure of said cuff according to a predetermined speed, said apparatus comprising:

a blood-flow-stopping means for stopping blood-flow at said upper-arm with said cuff;

a pressure-pulse-wave sensor, equipped being combined with said cuff to detect a pressure-pulse-wave appearing at an upper-stream side than the blood-flow stopped position; and a heart function parameter calculating means for calculating a heart function parameter of said living subject, based on said detected pressure-pulse-wave at said upper-stream side by said sensor, while said cuff is stopping the blood-flow of said upper-arm portion.

2. A blood-pressure measurement apparatus according to claim 1, wherein said heart-function calculating means calculates an ejection time ET as a time difference from a rising-point to a dicrotic notch, which are detected in said pressure-pulse-wave of said upper-stream side by said pressure-pulse-wave sensor.

3. A blood-pressure measurement apparatus according w claim 1, further comprising:

a plurality of electrodes to be stuck on predetermined positions of said living subject; and an electrocardiograph to detect, via said electrodes, electro-cardiac signals representing an activity-potential of cardiac muscle,
wherein, said heart-function parameter calculating means calculates, as a pre-ejection period PEP, a time difference from a time of a Q-wave of said electro-cardiac signal detected via said electrodes by said electrocardiograph to said rising-point of pressure-pulse-wave detected by said pressure-pulse wave sensor.

4. A blood-pressure measurement apparatus according to claim 3, wherein said heart-function parameter calculating means calculates a cardiac mechanical efficiency as a ratio of an aorta effective elastace Ea to a left ventricle tele-systolic elastance Ees based on said pre-ejection period PEP and said ejection time ET.

5. A blood-pressure measurement apparatus according to claim 1, wherein said apparatus comprises a plurality number of pressure-pulse-wave-sensors, which are arranged in a lengthwise direction at an inner peripheral face of said cuff.

6. A blood-pressure measurement apparatus according to claim 1, wherein said sensor comprises a plurality number of pressure sensitive semiconductor elements, which are arranged in a lengthwise direction at a pressing face of said sensor; and said apparatus comprises an optimum detective element determining means for selecting a most appropriate pressure sensitive semiconductor element from said pressure sensitive conductor elements.

7. A blood-pressure measurement apparatus according to claim 2, further comprising:

a plurality of electrodes to be stuck on predetermined positions of said living subject; and an electrocardiograph to detect, via said electrodes, electro-cardiac signals representing an activity-potential of cardiac muscle, wherein, said heart-function parameter calculating means calculates, as a pre-ejection period PEP, a time difference from a time of a Q-wave of said electro-cardiac signal detected via said electrodes by said electrocardiograph to said rising-point of pressure-pulse-wave detected by said pressure-pulse wave sensor.

\* \* \* \* \*